United States Patent [19]

Santilli et al.

[11] B 3,988,335
[45] Oct. 26, 1976

[54] 1-SUBSTITUTED-6-(2-SUBSTITUTED AMINOETHOXY)XANTHEN-9-ONES

[75] Inventors: Arthur A. Santilli, Havertown;
Anthony C. Scotese, King of Prussia;
Stanley C. Bell, Penn Valley;
Marvin E. Rosenthale, Havertown,
all of Pa.

[73] Assignee: American Home Products Corporation, New York, N.Y.

[22] Filed: May 8, 1974

[21] Appl. No.: 468,052

[44] Published under the second Trial Voluntary Protest Program on February 10, 1976 as document No. B 468,052.

[52] U.S. Cl. ............ 260/247.7 T; 260/247.5 H; 260/326.5 CA; 260/335; 424/248; 424/274; 424/283
[51] Int. Cl.² ........................... C07D 405/12
[58] Field of Search ............ 260/247.5 H, 247.7 T, 260/335, 326.5 CA

[56] References Cited
UNITED STATES PATENTS
3,555,043  1/1971  Archer .................. 260/335
3,597,420  8/1971  Archer .................. 260/335

FOREIGN PATENTS OR APPLICATIONS
776,555  4/1972  Belgium ................ 260/335

Primary Examiner—James A. Patten
Attorney, Agent, or Firm—Joseph Martin Weigman

[57] ABSTRACT

The disclosure is directed to 1,6-bis-(substituted oxy)-xanthen-9-ones which have the formula

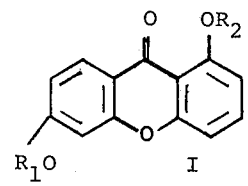

Where R₁ is morpholino(lower)alkyl, di(lower)alkylamino(lower)-alkyl, or pyrrolidinyl(lower)alkyl; and R₂ is lower alkylamino (lower)alkyl or hydrogen. The compounds are active as immunoregulators or as intermediates in the preparation of immunoregulators. The intermediates also have trichomonacidal activity.

4 Claims, 2 Drawing Figures

1-SUBSTITUTED-6-(2-SUBSTITUTED AMINOETHOXY)XANTHEN-9-ONES

This invention relates to new and useful 1,6-bis(substituted oxy)xanthen-9-ones and their pharmaceutically acceptable addition salts. The chemical structure of the compounds of the invention may be schematically represented by

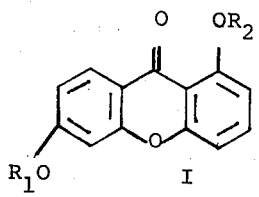

where $R_1$ is morpholino(lower)alkyl, di(lower)alkylamino(lower)-alkyl, or pyrrolidinyl(lower)alkyl; and $R_2$ is lower alkylamino (lower)alkyl or hydrogen.

The term "lower alkyl" and the like as used herein refers to straight chain and branched chain groups having 1 to 3 carbon atoms therein.

Specific embodiments of the invention are 1-hydroxy-6-(2-morpholinoethoxy)xanthen-9-one and 1-(2-diethylaminoethoxy)-6-(2-morpholinoethoxy)xanthen-9-one, dihydrochloride, hydrate.

Figure 1:
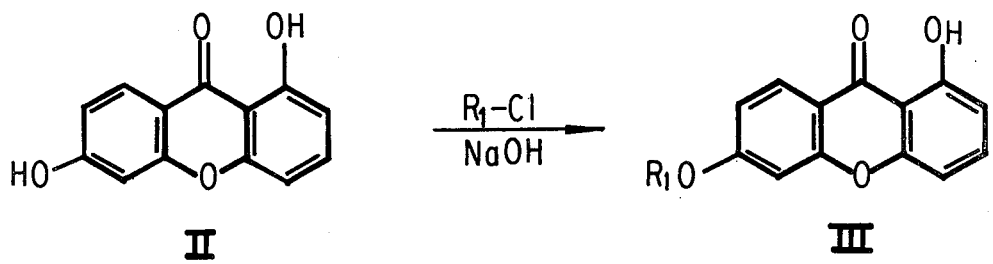
Figure 2:
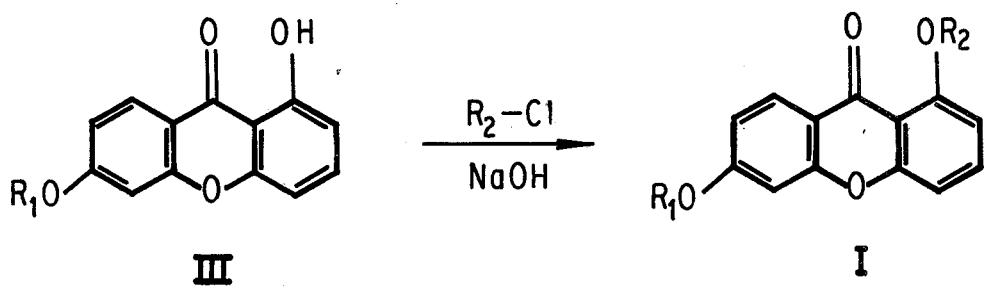

The preparation of the compounds of the invention may be represented by the flow diagram shown in FIGS. 1 and 2 where $R_1$ and $R_2$ are as defined above.

The closest known prior art is U.S. Pat. No. 2,732,373 and Belgium Pat. No. 776,555. Other prior art includes United States patent 3,597,420 and Netherlands Pat. Nos. 68,01093 and 72,03258.

The starting material 1,6-dihydroxy-9-oxoxanthene is described in P. K. Grover, G. D. Shah and R. C. Shah, *J. Chem. Soc.* 3982 (1966).

The 1-hydroxy-6-substituted xanthen-9-ones having formula III of FIG. 1 may be prepared as follows. A mixture of 1,6-dihydroxy-9-oxoxanthene, and a chloride of the desired $R_1$ substituent in a mixed organic and aqueous medium are heated in a basic medium for 5 to 24 hours. Preferably the mixture is refluxed for 20 hours. The layers are separated and the product recovered from the organic medium layer, for instance by drying, filtration, evaporation and recrystallization.

As shown in FIG. 2, substitution at the 1-position of the compounds of formula III may be accomplished as follows. A mixture in a basified aqueous-organic medium of a compound of formula III and an alkylating agent, such as 2-chlorotriethylamine, is heated under reflux for 4 to 8 hours with the water being removed by azeotropic distillation. The product is recovered from the reaction mixture, for instance by filtration, extraction, basifying, drying, acidying and recrystallization to provide a compound of formula I.

The test for the anti-inflammatory and immunosuppressive activity which characterizes immunoregulators is carried out as follows. Polyarthritis is induced in male Lewis strain rats (150–200 g.) by the injection of a suspension of tubercle bacilli in mineral oil in the subplantar tissue of the right hind paw. Drug therapy is either begun on the day of antigen or can be started after appearance of an established arthritic syndrome (14 days). Compounds are administered daily in the form of a fine suspension by stomach tube. Body weights, left and injected right paw volumes and occurrence of arthritic nodules on the ears, tail and front paws are determined at frequent intervals over a 14 to 21 day period. All animals are then autopsied and stress organ weights, hematology, histopathology and biochemical studies on blood proteins are done. Active compounds will either prevent or reverse the joint swelling and associated sequella of polyarthritis with minimal toxicity.

Compounds used as standards are Cortisone, phenylbutazone, indomethacin, aspirin, and 6-mercaptopurine. Literature references are: Newbould, B. B. Brit. *J. Pharm. Chemoth.* 21:127, 1963 and Rosenthale, M. E. and Nagra, L. *Proc. Soc. exp Biol. and Med.* 125: 149, 1967.

The compounds of formula I are active as immunoregulators. The compounds of formula III of FIG. 1 are useful in the preparation of compounds of formula I as is shown in FIG. 2. The compounds of formula III also have trichomonacidal activity.

In the pharmacological evaluation of the antiamebic activity of the compounds of this invention, the in vitro effects are tested as follows. The test substance is incorporated and diluted in the aqueous phase of modified Boeck-Drbohlav diphasic medium fortified with rice starch. The medium is inoculated with polybacteria, and a known number of trophozolites of *Endameba histolytica* NIH 200. After 48 hours incubation at 35°C. the trophozolites are counted. The minimal inhibitory concentration (MIC) expressed in micrograms per milliliter (μg/ml) is the least amount of a tested compound that completely inhibits *E. histolytica*. The activity of the compounds is compared against emetine hydrochloride as a standard. This procedure is suggested in Thompson et al. *Antibio. j Chemo.* 6 (1956) 337–50.

The assay of trichomonacidal activity in vitro is carried out as follows. A 12.5 milligram portion of test material (as based on the active moiety) is added to 2.5 milliliters (ml) of one percent phosphate buffer at pH 6. Further two-fold dilutions are made in the same buffer. A one milliliter volume of each dilution is transferred to small sterile screw cap assay tubes containing 3.8 milliliters of Diamond medium (formula furnished by American Type Culture Collection, Rockville, Md.) and 0.1 ml of calf serum. Each assay tube is inoculated with 0.1 milliliter of a 48–72 hour culture of *Trichomonas vaginalis* strain ATCC No. 13972. A control assay tube containing no test material is similarly inoculated. The assay tubes are gently shaken and then incubated for 48 hours at 30°C. Following incubation the tubes are gently shaken and with the aid of a Pasteur pipette a drop is deposited on a Spiers-Levy eosinophil counting chamber. The chamber is examined by phase contrast microscopy. The number of organisms present in one square millimeter is multiplied by 5000 in order to express the count per milliliter. The difference between the number of organisms present in the control tube and in the tubes containing the test material represents the relative potency of the test material and is expressed as the percentage kill at the specific dose level. Metronidazole may be used as a suitable positive control test material.

When the compounds of this invention are employed as described above, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay and so forth. They may be administered sublingually in the form of troches or lozenges in which the active ingredient is mixed with sugar and corn syrups; and then dehydrated sufficiently to make it suitable for pressing into a solid form. They may be administered orally in the form of solutions which may contain coloring and flavoring agents or they may be injected parenterally, that is intra-muscularly, intravenously or subcutaneously. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

In order more clearly to disclose the nature of the present invention, specific examples of the practice of the invention are hereinafter given. It should be understood, however, that this is done solely by way of example and is intended neither to delineate the scope of the invention nor limit the ambit of the appended claims. In the examples, all temperatures are stated in degrees centigrade, and the following abbreviations are used: "g" for grams, "ml" for milliliters, "min" for minutes, "hr" for hours, "Me" for Methyl, "Et" for ethyl, and "MPK" for milligram per kilogram of host body weight.

EXAMPLE I

This example illustrates the preparation of 1-hydroxy-6-(2-morpholinoethoxy)xanthen-9-one a compound of formula III:

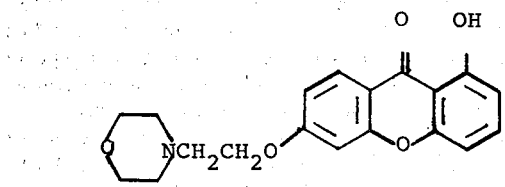

A mixture of 13.6 g of 1,6-dihydroxy-9-oxoxanthene, 37.0 g of N-(2-chloroethyl)-morpholine hydrochloride and 16.0 g of sodium hydroxide pellets was heated under reflux for 20 hours in a mixture of 960 ml of toluene and 240 ml of water. The layers were separated and the toluene layer was dried over magnesium sulfate, filtered and evaporated in a rotary evaporator. The residue was triturated with 100 ml of ethanol. The solid thus formed was collected and recrystallized from ethanol affording 4.2 g of product which melted at 134°–136°.

Based on the assumed molecular formula $C_{19}H_{19}NO_5$ it was calculated that the elemental analysis by weight would be 66.85 percent carbon, 5.61 percent hydrogen and 4.10 percent nitrogen. The product was analyzed and found to contain 66.72 percent carbon, 5.61 percent hydrogen and 4.14 percent nitrogen which confirmed the accuracy of the assumed formula. This may be expressed:

Anal. Calcd for $C_{19}H_{19}NO_5$: C, 66.85; H, 5.61; N, 4.10. Found: C, 66.72; H, 5.61; N, 4.14.

When evaluated in the foregoing test for anti-inflammatory activity the compound was found to provide 5 percent protection against acute inflammations at a dose of 100 MPK.

When evaluated in the foregoing test for trichomonacidal activity the compound was found to produce a 99 percent kill at 1 milligram per kilogram.

EXAMPLE II

This example illustrates the preparation of 6-(2-dimethylamino-1-methylethoxy)-1-hydroxyxanthen-9-one, hydrochloride, a compound of formula III:

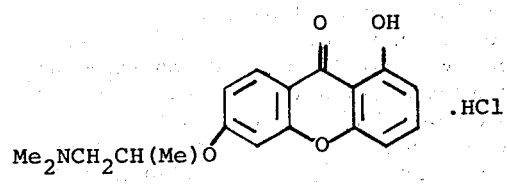

A mixture of 13.68 g of 1,6-dihydroxy-9-oxoxanthene, 18.96 g of 2-chloro-N,N-dimethylpropylamine hydrochloride and 9.6 g of sodium hydroxide pellets was heated under reflux for 20 hours in a mixture of 960 ml of toluene and 240 ml of water. The toluene layer was dried over magnesium sulfate, filtered and evaporated in a rotary evaporator. The residue was dissolved in ethanol and acidified with an alcoholic hydrochloric acid solution. The mixture was diluted with petroleum ether until just the cloudy point. The precipitate thus formed was collected and recrystallized from ethanol to give 1.35 g of product which decomposed at 246°–249°.

Anal. Calcd for $C_{18}H_{20}ClNO_4$: C, 61.80; H, 5.76; N, 4.00. Found: C, 61.49; H, 5.88; N, 3.95.

When evaluated in the foregoing test for trichomonacidal activity the compound was found to produce a 99 percent kill at 100 micrograms per milliliter and a 100 percent kill at 1 milligram per milliliter.

EXAMPLE III

This example illustrates the preparation of 1-hydroxy-6-[2-(1-pyrrolidinyl)ethoxy]xanthen-9-one, hydrochloride, a compound of formula III:

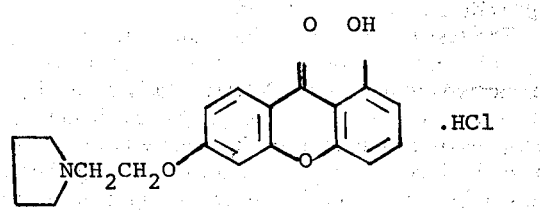

A mixture of 13.68 g of 1,6-dihydroxy-9-oxoxanthene, 20.40 g of N-(2-chloroethyl)-pyrrolidine hydrochloride and 9.8 g of sodium hydroxide pellets was refluxed for 20 hours in a mixture of 960 ml of toluene and 240 ml of water. The toluene layer after drying over magnesium sulfate was evaporated in a rotary evaporator. The solid residue was recrystallized from ethyl acetate. This pure free base was dissolved in boiling ethanol and acidified with alcoholic hydrochloric acid solution. The precipitate was collected and washed with ether giving 2.0 g of product which decomposed at 260°–264°.

Anal. Calcd for $C_{19}H_{20}ClNO_4$: C, 63.07; H, 5.57; N, 3.87. Found: C, 62.76; H, 5.79; N, 3.85.

When evaluated in the foregoing test for trichomonacidal activity the compound was found to produce a 16 percent kill at 100 micrograms per milliliter and a 100 percent kill at 1 milligram per milliliter.

EXAMPLE IV

This example illustrates the preparation of 6-(2-dimethylaminoethoxy)-1-hydroxyxanthen-9-one, hydrochloride, a compound of formula III:

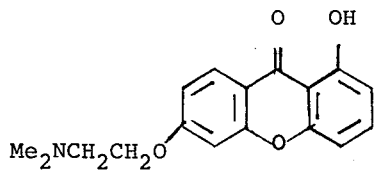

To a stirred suspension of 13.68 g of 1,6-dihydroxy-9-oxoxanthene in 1000 ml of xylene was added 9.6 g of 50 percent sodium hydroxide. A mixture of 17.28 g of 2-dimethylaminoethyl chloride hydrochloride and 9.6 g of 50 percent sodium hydroxide in 20 ml of water was then added. The mixture was refluxed for 6 hours with the water being removed by azeotropic distillation. After six hours the mixture was filtered and the filtrate extracted with 350 ml of warm 10 percent aqueous hydrochloric acid solution. The water layer was basified with ammonium hydroxide and the precipitate thus formed was collected and recrystallized from heptane. This pure free base was dissolved in 200 ml of ether and acidified with alcoholic hydrochloric acid solution affording 1.45 g of product which decomposed at 247°–250°.

Anal. Calcd for $C_{17}H_{18}NO_4Cl$: C, 60.81; H, 5.40; N, 4.17. Found: C, 60.42; H, 5.51; N, 3.99.

When evaluated in the foregoing test for trichomonacidal activity the compound was found to produce a fifty percent kill at 100 micrograms per milliliter and a 100 percent kill at 1 milligram per milliliter.

When evaluated in the foregoing test for antiamebic activity the compound was found to produce a 93 percent kill at 1 milligram per milliliter (emetine 1.95).

EXAMPLE V

This example illustrates the preparation of 1-(2-diethylaminoethoxy)-6-(2-morpholinoethoxy)xanthen-9-one, dihydrochloride, hydrate, a compound of formula I:

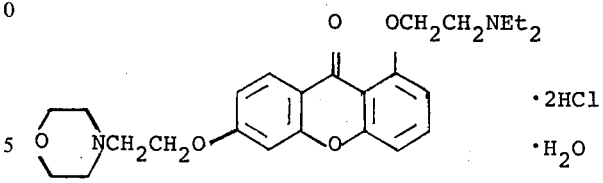

A mixture of 3.4 g of 1-hydroxy-6-(2-morpholinoethoxy)-xanthen-9-one, 1.7 g of 2-chlorotriethylamine hydrochloride and 1.6 g of 50 percent sodium hydroxide was heated under reflux in 500 ml of xylene for 6 hours with the water being removed by azeotropic distillation. The reaction mixture was filtered and the filtrate extracted with 250 ml of 10 percent aqueous hydrochloric acid solution. The water layer was basified with concentrated ammonium hydroxide to pH 9 and extracted with 250 ml of ether. The ether layer was dried over magnesium sulfate, filtered and after dilution with 25 ml of ethanol was acidified with ethereal hydrochloric acid solution. The precipitate was collected and the filter cake quickly dried and recrystallized from ethanol with ether used for inducing precipitation to give 0.4 g of product which decomposed at 269°–271°.

Anal. Calcd for $C_{25}H_{36}N_2O_6Cl_2$: C, 56.50; H, 6.83; N, 5.27. Found: C, 56.74; H, 6.65; N, 5.35.

The compound showed 46 percent protection against acute inflammation at a dose of 75 milligrams per kilogram of host body weight (MPK) and 73 percent protection against delayed inflammation and 94 percent protection against delayed hypertension at the same dose level when tested as described above.

What is claimed is:
1. 1-Hydroxy-6-(2-morpholinoethoxy)xanthen-9-one.
2. 6-(2-Dimethylamino-1-methylethoxy)-1-hydroxyxanthene-9-one, hydrochloride.
3. 1-Hydroxy-6-[2-(1-pyrrolidinyl)ethoxy]xanthen-9-one, hydrochloride.
4. 6-(2-Dimethylaminoethoxy)-1-hydroxyxanthen-9-one, hydrochloride.

\* \* \* \* \*